Figure 1:
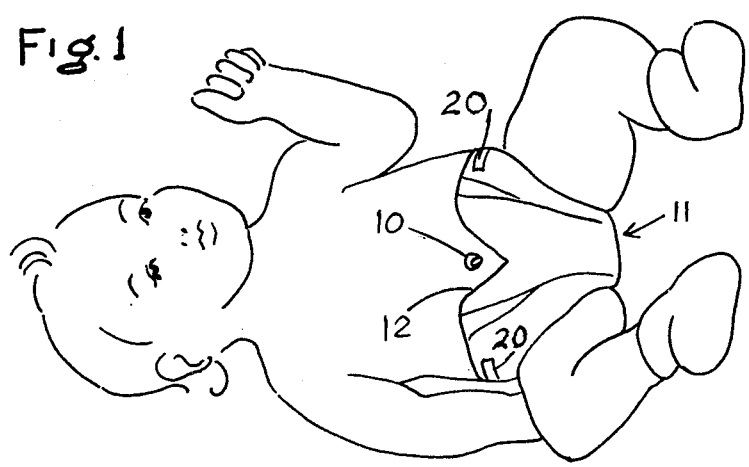

United States Patent [19]

Mehta

[11] 4,230,113
[45] Oct. 28, 1980

[54] INFANT'S DIAPER

[76] Inventor: Khusal Mehta, T2-6 Hatfield Village Apts., Hatfield, Pa. 19440

[21] Appl. No.: 924,917

[22] Filed: Jul. 17, 1978

[51] Int. Cl.³ .............................................. A61F 13/16
[52] U.S. Cl. ................................................ 128/287
[58] Field of Search ................ 128/284, 286, 287, 288

[56] References Cited

U.S. PATENT DOCUMENTS

| 395,411 | 1/1889 | Wiley | 128/288 |
|---|---|---|---|
| 2,684,677 | 7/1954 | Pinney | 128/284 |
| 3,863,637 | 2/1975 | MacDonald et al. | 128/287 |
| 3,916,447 | 11/1975 | Thompson | 128/287 |

OTHER PUBLICATIONS

*Baby Talk,* vol. XV, issue #1, p. 3, Jan. 1950.

*Primary Examiner*—C. Fred Rosenbaum
*Attorney, Agent, or Firm*—Raymond Underwood

[57] ABSTRACT

An infant's diaper has a notch centrally located along one of its narrow edges to thereby expose the navel area and eliminate diaper contact with the umbilicus of newborn and low weight babies.

1 Claim, 6 Drawing Figures

U.S. Patent  Oct. 28, 1980  4,230,113

INFANT'S DIAPER

This invention relates to diapers and especially to diapers which are particularly adapted to newborn infants and more particularly to premature infants. The feature of the invention is the exposure of the umbilicus of the diapered infant.

Newborn infants are exceptionally prone to inflammation and infection and colonization of bacteria at the umbilicus as the residual, freshly cut umbilical cord offers an inviting site for bacterial invasion and frictional irritation by the overlying diaper. The rubbing movement of the conventional diaper on an umbilicus which is still raw, as the infant squirms, kicks and moves, often produces a sore place which causes the infant to be quite fretful. The umbilical area is noticeably reddish and inflammed.

Also, the overlying diaper can serve as a carrier of bacteria to the unhealed, cut cord and bring about an infection. When the conventional diaper becomes contaminated with faeces and urine the body movements of the infant can advance these waste materials to the navel area and initiate a diseased site at the cord terminus. The infant's faeces and urine may contain *E. coli* and group B Staph. as well as other pathogenic organisms and they can move along the diaper and through its linings and frequently infect the open flesh of the umbilical cord.

The probability of such morbid conditions is likely to be more prevalent in premature and under-weight newborn infants due to their lower resistance to an adverse situation or environment. It is obviously more important to prevent the initiation of such inflammations and infections in these susceptible infants than it is to permit the adverse condition to develop and then try to cure the complaint. The application of an adhesive bandage to the already tender skin around the navel to prevent the frictional rub of the diaper is obviously objectionable. Or, if an infection has developed the uncertainty of the selection of and the final effectiveness of an antibiotic or other germicidal agent shows that the elimination of the causative factor is much to be desired.

In accordance with the present invention the portion of the diaper which would overlie the umbilicus, if an intact conventional diaper were used, is cut away. The diaper itself may be as simple as an absorbant cloth or sheet material or as complex as the present day multi-layer, pin-less, disposable diaper. The invention, in its essential feature, involves the elimination of the portion which would be over the navel area if it were not removed. This cutaway part may be V-shaped, a U-shaped or other shaped notch which opens centrally of the width of the top edge of the front panel of the diaper.

Figure 2:
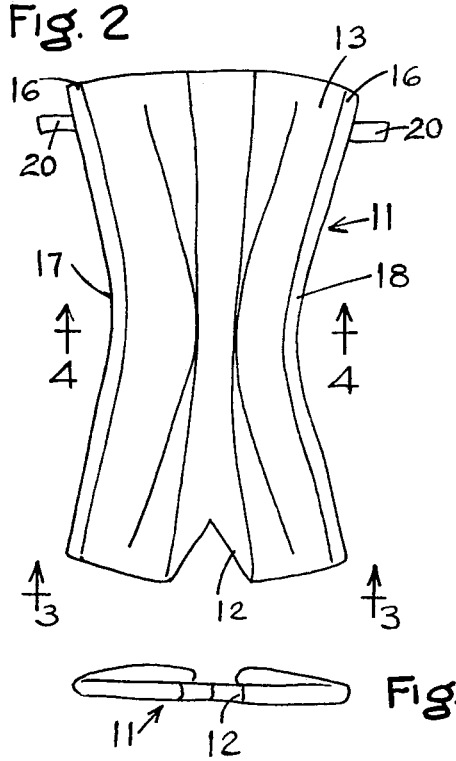
Figure 5:
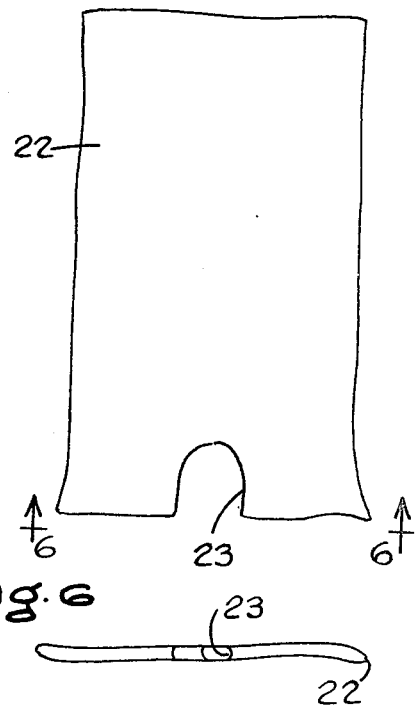
Figure 3:
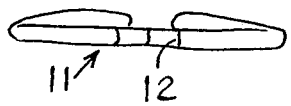
Figure 6:
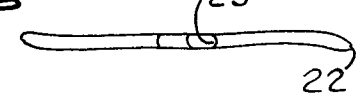
Figure 4:
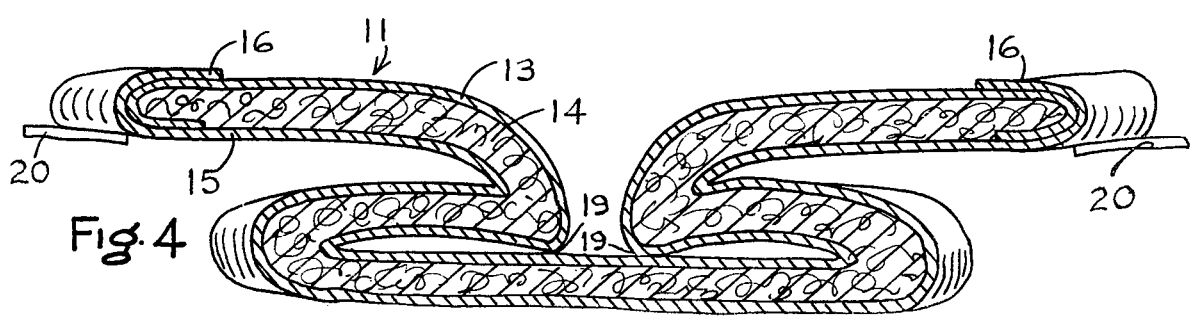

Representative embodiments of the invention are illustrated in the accompanying drawings in which:

FIG. 1 is a plan view of an infant to which a preferred form of the invention has been applied, FIG. 2 is a plan view of the preferred diaper of FIG. 1, FIG. 3 is an end view on the line 3—3 of FIG. 2, FIG. 4 is a sectional view on the line 4—4 of FIG. 2 but on an enlarged scale, FIG. 5 is a plan view of a simplified embodiment of the invention and FIG. 6 is an end view on the line 6—6 of FIG. 5.

FIG. 1 shows a reclining infant having the freshly cut umbilicus 10, to which the diaper of FIGS. 2, 3 and 4 has been applied. The diaper is generally indicated by the reference numeral 11 and it is to be noted that it has the triangular or V-shaped notch 12 which leaves the navel area exposed. The usual squirming and movement of a newborn infant will not bring the diaper into contact with the newly cut and unhealed umbilical cord remaining on the infant. The base of the triangle opens at one of the narrow ends of the diaper about centrally of the width of the edge.

As the feature of the invention is the notch in the top edge of the applied diaper it is apparent that the detailed construction of the diaper is relatively unimportant. To furnish a complete illustration of the invention, one possible construction is shown in FIGS. 2–4 but it is to be understood that the invention is not limited to the details shown and that the notch can be formed in conventional, marketed diaper and also in any cloth or fabric material formed and intended to be used as a diaper.

The diaper 11 is made up of the inner layer 13 which is to go next to the infant's skin. It must be moisture transmitting and it preferably is of cotton sheeting or like fabric material which will be gentle to the infant's skin. It may even be a moisture transmitting plastic with a multiplicity of minute holes through it.

The intermediate layer 14 should be highly moisture absorbent and suitable material is wadding, fibrous material such as cotton and cellulose. Synthetic, sponge-like material would be satisfactory. It should serve to spread the moisture throughout the layer 14.

The outer layer 15 which is to be away from the infant's skin should be moisture impervious. This may be waterproofing treated cotton sheeting or synthetic fabric material such as nylon or polyester which will not transmit moisture through it. Sheets of vinyl plastic may in fact be used.

The inner layer 13 is shown to be larger all around than the intermediate layer 14 so that its edge can be turned around the middle layer 14 as is shown in FIG. 4. The outer layer 15 is also large enough so that its edge can be brought around the diaper edge as shown at 16 to help keep moisture within the layer 14. The edge at 16 may be slightly glued to hold it down and in place.

The diaper 11 in broad outline is an elongated rectangle which is about one and a half times longer than it is wide. Its two long sides are folded inwardly about midway of their lengths as shown at 17 and 18 to form a central pleat which reduces the central width of the diaper where it lies between the legs. The pleats are slightly glued at 19 so that they can be easily opened if desired.

The notch 12 is cut out centrally of the edge at one of the narrow ends and as is shown in FIG. 2 it is a triangle with the apex pointing directly inwardly. This V-notch extends inwardly from the edge more or less half way to the penis area of the infant to which it is applied. The notch must be deep enough to make sure that the navel will be exposed despite the movements of the infant but it must not be so deep that it exposes the urethra opening.

The diaper is applied to the infant in the usual manner and so that the cut away notch exposes the navel. The diaper can be pinned to hold it in place on the infant but the tabs 20 may be provided in known manner so that their pressure sensitive, self-adhering surfaces will hold the diaper in closed position on the infant.

FIGS. 5 and 6 show a most simple modification of the invention as the diaper material is a single rectangular sheet of so called diaper cloth or it may be of a like moisture absorbent material. One narrow end has a U-shaped notch 23 cut centrally into it so that when it is applied the infant's navel area will be exposed as is shown in FIG. 1. As is stated above there is no overlying diaper material to rub on and irritate the unhealed umbilicus or to carry body wastes to it.

Other variations in the notch will be obvious; for instance the V-shaped and the U-shaped notches may be interchanged. The notch can be somewhat narrow as it will open up when the diaper is applied to an infant. It is necessary to avoid a hole in the diaper which leaves the edge intact because if the diaper moves downwardly such an intact edge could overlie and contact the residual umbilical cord.

The diaper of this invention eliminates the irritation and infection caused by an overlieing diaper and consequently it eliminates the present practice in hospitals of treating the sore umbilicus with antibiotics and taking cultures. The diaper will save the use of and cost of antibiotics and cultures and will eliminate the toxicity of some drugs. It will thus avoid prolonged hospital stays due to this cause.

The marked reduction in umbilicus problems in newborns means that there is a reduced concern by the parents and nursery staff. The diaper might prevent umbilical granuloma. It is very easy to apply it to premature and low birth weight babies. Also, the material that is saved by providing the notch can mean a cost reduction in making the notched diaper. These advantages together with the hygienic and non irritating benefits of the diaper of this invention explain the outstanding utility of the notched diaper.

The dimensional size of the notch is dependent on the size of the diaper, which in turn is dependent on the size of the infant. The diaper for a premature or a low birth weight baby weighing up to five or six pounds would be generally about 22 cm. wide and 27 cm. long. The notch would be about 4 to 6 cm., preferably about 5 cm. wide where it opens at the edge of the narrow edge of the diaper and the notch would be from 2.5 to 4.5 cm., preferably about 3.5 cm. deep from that edge.

For a larger diaper for a bigger baby the width may be about 25 cm. and the length may be about 34 cm. The mouth of the notch would then be from about 5 to 7 cm., preferably about 6 cm. wide and would be from about 2.5 to 5 cm., preferably about 4 cm. deep. A more general rule, as is mentioned above, is that the notch would extend into the diaper so that it is about half way between the umbilicus and the symphysis pubis.

I claim:

1. A moisture absorbing infant's diaper for newborn babies, comprising an outer water impervious layer, an intermediate moisture absorbing layer and an inner moisture transmitting layer, the two long sides being folded inwardly about midway of their lengths to form a central pleat which reduces the central width of the diaper, which is about 22 cm. wide, about 27 cm. long and has in one of its narrow ends a V-shaped notch which opens out at that edge of the diaper, said notch being centrally located along that end and being from 2.5 to 4.5 cm. deep and from 4 to 6 cm. wide at the edge.

* * * * *